(12) United States Patent
Friedman et al.

(10) Patent No.: US 6,358,213 B1
(45) Date of Patent: Mar. 19, 2002

(54) CALCULATION OF QUALITY AND ITS USE IN DETERMINATION OF INDIRECT NONINVASIVE BLOOD PRESSURE

(75) Inventors: Bruce Friedman; Lawrence T. Hersh; Richard Medero, all of Tampa, FL (US)

(73) Assignee: Critikon Company, LLC, Tampa, FL (US)

( * ) Notice: Subject to any disclaimer, the term of this patent is extended or adjusted under 35 U.S.C. 154(b) by 0 days.

(21) Appl. No.: 09/376,854

(22) Filed: Aug. 18, 1999

(51) Int. Cl.⁷ .................................................. A61B 5/00
(52) U.S. Cl. ........................ 600/493; 600/494; 600/495
(58) Field of Search ............................. 600/493.6, 490

(56) References Cited

U.S. PATENT DOCUMENTS

| | | | |
|---|---|---|---|
| 4,360,029 A | 11/1982 | Ramsey, III ................. 128/681 |
| 4,461,266 A | 7/1984 | Hood, Jr. et al. ............ 128/681 |
| 4,543,962 A | 10/1985 | Medero et al. ............... 128/682 |
| 4,546,775 A | 10/1985 | Medero ....................... 128/681 |
| 4,638,810 A | 1/1987 | Ramsey, III et al. ........ 128/681 |
| 4,754,761 A | 7/1988 | Ramsey, III et al. ........ 128/683 |
| 4,777,959 A | * 10/1988 | Wallach et al. .............. 600/493 |
| 5,052,397 A | 10/1991 | Ramsey, III et al. ........ 128/682 |
| 5,170,795 A | 12/1992 | Ramsey, III et al. ........ 128/682 |
| 5,337,750 A | * 8/1994 | Walloch ....................... 600/494 |
| 5,385,149 A | * 1/1995 | Chang et al. ................ 600/493 |
| 5,518,000 A | 5/1996 | Booth et al. ................. 128/680 |
| 5,542,428 A | * 8/1996 | Jayne .......................... 600/494 |
| 5,577,508 A | 11/1996 | Medero ....................... 128/681 |
| 5,579,776 A | 12/1996 | Medero ....................... 128/680 |
| 5,590,662 A | 1/1997 | Hersh et al. ................. 128/681 |
| 5,704,362 A | 1/1998 | Hersh et al. ................. 128/680 |

* cited by examiner

Primary Examiner—Robert S. Nasser, Jr.
(74) Attorney, Agent, or Firm—Larry L. Saret; Michael Best & Friedrich LLC

(57) ABSTRACT

An automated sphygmomanometer which utilizes quality algorithms to stop any further analysis at various points during a blood pressure determination because of corrupted data. If the data is so corrupted that giving blood pressure numbers is inappropriate, this is recognized and the determination stopped. The quality algorithms make a decision to get more data with the hope of improving the blood pressure estimation. The request for data occurs both before and/or after a curve fitting process, if such a process is utilized. Some information is also provided to the cuff pressure control function about which pressure levels would be best for gathering the additional data. The quality algorithms are also used to make a decision as to whether it is appropriate to publish the blood pressure values obtained. Control parameters (weights) may be set within the blood pressure algorithm to help with other aspects of the NIBP algorithm and improve the quality of the final published numbers. The quality algorithms may also help the system to decide whether to publish any warnings when significant artifact is present.

31 Claims, 10 Drawing Sheets

CALCULATION OF QUALITY AND ITS USE IN DETERMINATION OF INDIRECT NONINVASIVE BLOOD PRESSURE

FIELD OF THE INVENTION

This invention relates to automated blood pressure monitoring, and more particularly, to automated blood pressure monitors that use a signal quality measurement in determining whether a noninvasive blood pressure measurement using that signal is reliable.

BACKGROUND OF THE INVENTION

Automated oscillometric blood pressure monitors are known in the art in which a curve is computationally fitted to the oscillometric envelope defined by the amplitudes of complexes at varying cuff pressures, thereby enabling mean arterial pressure (MAP) and systolic and diastolic blood pressures to be more accurately computed. As explained in U.S. Pat. No. 5,704,362, such curve fitting computations are inherently immune to aberrations caused by artifacts. Generally, such a technique calls for a Gaussian-shaped function to be computationally model fitted to the oscillometric envelope, although other functions could be used. The curve-fitting computations employ the Marquardt method which is a combination of the steepest descent on a sum-squared error function and Gauss-Newton zero-finding for an observation function. The method described in U.S. Pat. No. 5,704,362 constrains the envelope to the known reasonable shape of the Gaussian function, thereby providing a filtering method which makes the curve fitting less dependent upon any single data point. This allows artifact detection techniques during data gathering to be relaxed or eliminated. Also, the envelope data may include historical data collected over several blood pressure determinations and weight-averaged to provide weight-averaged prediction of the next blood pressure determination.

The Gaussian curve fitting method employed in U.S. Pat. No. 5,704,362 determines a set of three parameters based on data from the present or from previous blood pressure determinations, these parameters including the envelope amplitude (A), the mean (B), and the deviation from the mean (C). In other words, the Gaussian curve is defined by its amplitude, mean, and deviation, and the curve fit is defined as the curve with the amplitude, mean, and deviation which minimizes the sum-squared error (s.s.e.) between the Gaussian curve and the data points at each of the raw envelope pressures. A search is conducted in the (A,B,C) variable space until a minimization point is found. Data from the current blood pressure determination may be used to shift the Gaussian curve from a previous determination to the correct pressure vicinity so that it more closely fits the most recently measured data. This can help with identifying the amplitude of raw blood pressure complexes and rejecting artifact. Further details regarding the curve fitting method described in U.S. Pat. No. 5,704,362 are hereby incorporated by reference.

Unfortunately, even such curve fitting techniques must address the problem that patient motion, vibrations, and other interference may cause artifact in the pressure signal obtained from the cuff during the blood pressure determination. When this happens, identifying blood pressure complexes and their properties is troublesome, even when using the above-referenced curve-fitting techniques. It can then be difficult to decide when to publish blood pressure results and when to give warnings that artifact is present or that the output may be inaccurate. The present invention relates to systems and methods which have been developed to handle this problem.

SUMMARY OF THE INVENTION

The present invention addresses the afore-mentioned problems in the art by using objective criteria to determine the quality and reliability of the measured NIBP data prior to presenting the data to the monitor's display for viewing. In accordance with the invention, the oscillometric envelope data is checked for shape, quality of curve fit (if a curve fit procedure is used), history quality, envelope quality, complex quality, and step quality. These quality values are then combined into an overall quality value that is used to determine whether or not to publish the gathered oscillometric envelope data and whether messages warning of artifacts should also be given.

In particular, the present invention relates to a method of measuring the blood pressure of a subject, comprising the steps of:

obtaining from the subject a plurality of oscillometric data values from an amplitude of at least one complex taken at a plurality of pressure levels, the oscillometric data values representing points of an oscillometric envelope defined by measured blood pressure oscillations;

calculating the patient's blood pressure from the oscillometric data values;

checking the signal quality of the oscillometric data values; and selectively displaying the calculated blood pressure in accordance with the signal quality of the oscillometric data values.

The method of the invention is implemented by an automated sphygmomanometer apparatus comprising an inflatable and deflatable pressure cuff, an inflating apparatus coupled to the cuff so as to selectively apply a medium under pressure to the cuff for inflating and pressurizing the cuff, a cuff pressure sensor coupled to the cuff so as to sense cuff pressure including any blood pressure oscillations therein, a deflating apparatus coupled to the cuff so as to selectively relieve pressure from the cuff, and a programmed control device responsive to a cuff pressure determination of the cuff pressure sensor. In accordance with a preferred embodiment of the invention, the control device is programmed to control the inflating apparatus to inflate the cuff and the deflating apparatus to deflate the cuff during respective blood pressure determinations of a patient at predetermined intervals and to store oscillometric envelope data representing points of an oscillometric envelope defined by measured blood pressure oscillations. Also, the control device is further programmed to calculate the patient's blood pressure from the oscillometric envelope data, to check the signal quality of the oscillometric envelope data, and to selectively display the calculated blood pressure in accordance with the signal quality of the oscillometric envelope data.

The programmed control device checks the signal quality of the oscillometric envelope data in accordance with the invention by determining if the oscillometric envelope has a predetermined general bell shape, by using blood pressure results determined during implementation of a curve fit procedure (if used) to the oscillometric envelope data to determine if the calculated blood pressures are such that diastolic<MAP<systolic and in a reasonable physiological range, by comparing newly acquired oscillometric envelope data with stored oscillometric envelope data and determining an intermediate history quality number as a percentage of values of the newly acquired oscillometric envelope data that are within a predetermined range from values of the stored oscillometric envelope data, by determining an intermediate envelope quality number as a measure of how well curve fit data used by the curve fit procedure fits the newly acquired oscillometric envelope data, by determining an intermediate complex quality number as a measure of a percentage of pressure steps whose best complexes are above an estimated noise level that is a root mean square (r.m.s.) error of all complexes in the newly acquired oscillometric envelope data, and/or by determining an intermediate step quality number as a measure of the variability of sizes of complexes at an envelope step pressure level. Preferably, these values are combined in accordance with a weighting function to create an overall quality number representative of the signal quality of the oscillometric envelope data. Generally, more recent oscillometric envelope data is weighted more heavily than older oscillometric envelope data.

In a preferred embodiment, the programmed control device determines the intermediate envelope quality number using the equation:

Intermediate envelope quality=$A*100/(A+\text{sqrt}(WEIGHT*\text{Envelope s.s.e.}))$ where A is a Gaussian parameter for amplitude used by the curve fit procedure, WEIGHT has a value based on the intermediate history quality number, and envelope sum-squared error (s.s.e.) is found using the following equation:

Envelope s.s.e.=$\Sigma(a_i - A \cdot e^{-(P_i-B)2/C})^2$ where "$a_i$" and "$p_i$" represent the oscillometric envelope data and correspond to step oscillation amplitude and step pressure, respectively, "i" is an index used for envelope step data, and B and C are Gaussian parameters for mean, and deviation, respectively, used by the curve fit procedure. The programmed control device also bases the estimated noise level on a complex s.s.e. determined from the following equation:

$$\text{complex s.s.e.} = \sum_{i,j} \left(c_{ij} - A \cdot e^{-(p_i-B)^2/C}\right)^2$$

where $c_{ij}$ is complex data representing complex size from the newly acquired oscillometric envelope data, "i" is an index used for envelope step data, j is an index for the complexes at an envelope step pressure level, $p_i$ represents step pressure, and A, B, and C are Gaussian parameters for amplitude, mean, and deviation, respectively, used by the curve fit procedure.

In the preferred embodiment, the programmed control device determines the intermediate step quality number as a percentage of complexes, out of all complexes received, which has a ratio (an absolute difference between each complex to a best estimate of complex size for the cuff pressure at which the complex occurs) which exceeds a threshold dependent upon the intermediate history quality number.

Preferably, the programmed control device checks the calculated blood pressure and the overall quality number to determine if the calculated blood pressure and the overall quality number make physiological sense prior to displaying the calculated blood pressure. Then, the programmed control device compares the overall quality number to a first threshold, whereby the oscillometric envelope data is displayed only if the first threshold is exceeded. The programmed control device may also compare the overall quality number to a second threshold, greater than the first threshold, whereby the oscillometric envelope data is displayed with a message warning of artifact if the overall quality number exceeds the first threshold but not the second threshold and displays the oscillometric envelope data without the warning message if the overall quality number exceeds both the first and second thresholds.

The scope of the invention also includes corresponding methods as apparent from the following detailed description of the invention.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENTS

A system and method which meets the above-mentioned objects and provides other beneficial features in accordance with the presently preferred exemplary embodiment of the invention will be described below with reference to FIGS. 1–9. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

In U.S. Pat. No. 4,360,029, Ramsey discloses in great detail a system for oscillometric blood pressure monitoring to which the principles of the present invention may be applied with advantage. The disclosure of the commonly assigned Ramsey '029 patent is incorporated by reference herein. The following description of FIG. 1 will act as a brief summary of the operation of that system.

Figure 1:
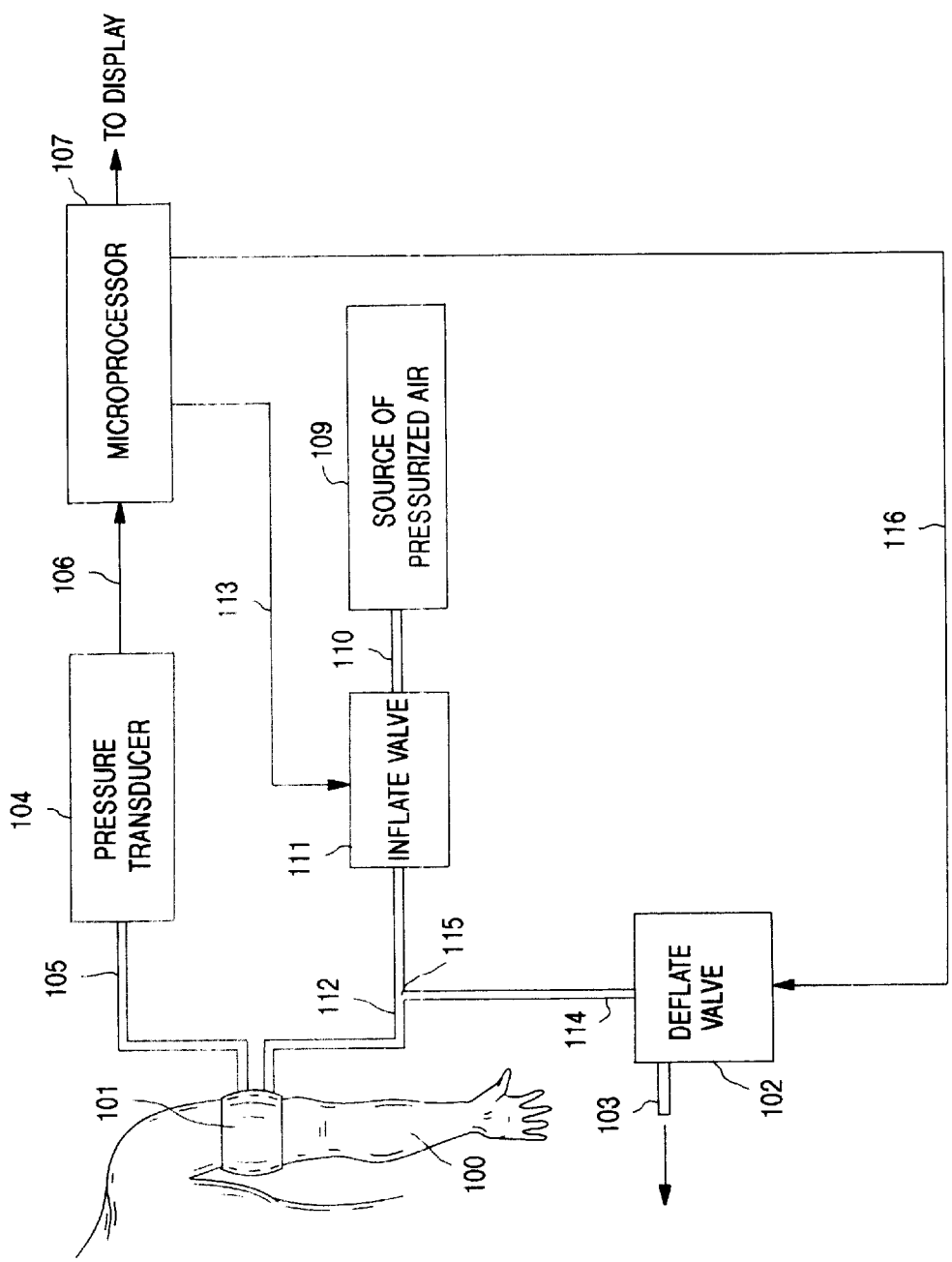
FIG. 1 is a high level diagram of a NIBP monitoring system in accordance with the invention.

In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. As will be described more fully below, the deflation of cuff 101 via deflate valve 102 is controlled by microprocessor 107 via control line 116.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

From the standpoint of the principles of the present invention, the processing of the signals from pressure transducer 104 by the microprocessor 107 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. Nos. 4,543,962, of Medero in 4,546,775, of Hood, Jr. et al. in 4,461,266, of Ramsey, III et al. in 4,638,810, of Ramsey, III et al. in 4,754,761, of Ramsey, III et al. in 5,170,795, of Ramsey, III et al. in 5,052,397, of Medero in 5,577,508, and of Hersh et al. in 5,590,662, all of which are commonly assigned herewith and the disclosures of which are hereby incorporated by reference. In any event, it is desirable to use any of the known techniques to determine the quality of the oscillation complexes received at each level so that the blood pressure determination is made using actual blood pressure data and not artifacts.

The apparatus of the present invention described above with reference to FIG. 1, except for the programming of the microprocessor 107, can be substantially the same as that disclosed in the Ramsey, III et al. '029 and '034 patents. Thus, during operation of the apparatus illustrated in FIG. 1, it can be assumed that air under pressure to, for example, about 8–10 p.s.i. is available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine.

As noted above, actual measurement of the blood pressure under the control of the microprocessor 107 and the deflate valve 102 as sensed by pressure transducer 104 can be accomplished in any suitable manner such as that disclosed in the aforementioned patents. In addition, the deflation of the cuff 101 can be controlled as described by Booth et al. in U.S. Pat. Nos. 5,518,000 and by Medero in 5,579,776, also assigned to the present assignee and the contents of which are hereby incorporated by reference in their entireties. At the completion of each measurement cycle, the deflate valve 102 can be re-opened long enough to relax the cuff pressure substantially completely via exhaust 103. Thereafter, the deflate valve 102 is closed for the start of a new measurement cycle.

By way of a summation, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 116 from microprocessor 107 and the blood pressure measurement taken.

Figure 2:
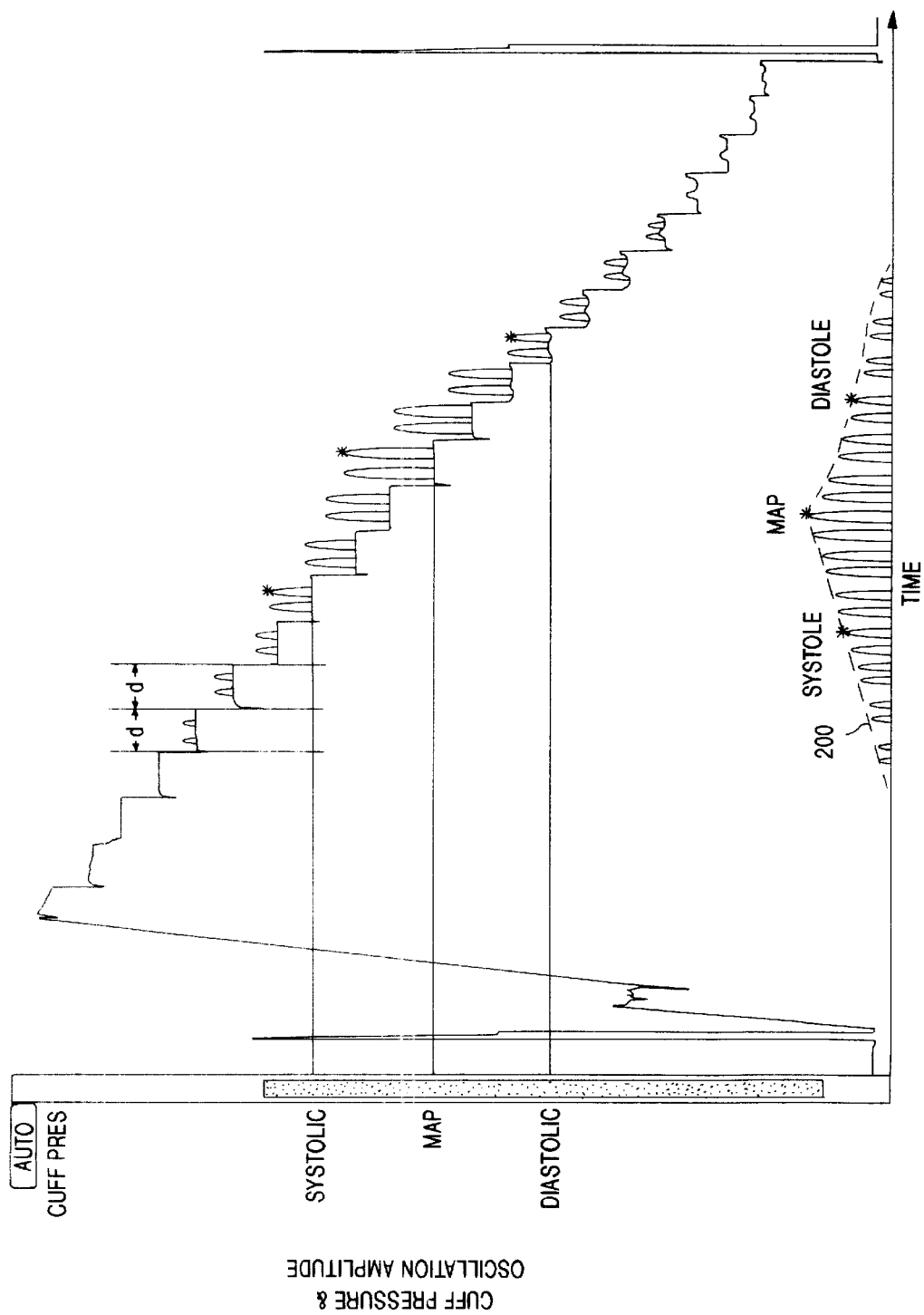
FIG. 2 illustrates oscillometric data including step deflate and complexes derived using the NIBP monitoring system of FIG. 1.

In typical automatic sphygmomanometric devices, the cuff deflation operation is accomplished in equal decrements, usually about 8 mm Hg per step. FIG. 2 illustrates a pressure versus time graph illustrating a conventional cuff step deflation and measurement cycle for a conventional NIBP monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP and/or the oscillometric envelope 200 may be determined. The entire blood pressure determination process is repeated at predetermined set intervals, which are typically set by the user.

To this point, the FIG. 1 monitor operates in a conventional manner. In accordance with the invention, it is desired to modify such a system to determine the quality of the gathered signal to then determine whether the data included in that signal is reliable. The signal quality is determined by algorithms (described below) implemented by microprocessor 107 used during the gathering of data and the subsequent calculation of blood pressure to help assure results are of an accuracy sufficient for clinical use. To do this, an evaluation is made as to the physiological reasonableness of the raw data, the amount of noise in the raw data, and the physiological likelihood of the final result.

In accordance with the invention, the quality algorithms are utilized in microprocessor 107 to stop any further analysis (at various points during a blood pressure determination) because of corrupted data. If the data is so corrupted that giving blood pressure numbers is inappropriate, this should be recognized and the determination stopped. This will help keep the quality of the blood pressure numbers high when they do get published. The quality algorithms of the invention are also used to make a decision to get more data with the hope of improving the blood pressure estimation. The request for additional raw envelope data should later lead to higher overall quality and publishable blood pressure numbers. The request for data could occur both before and/or after the afore-mentioned curve fitting process, if such a process is utilized. It would also include providing some information to the cuff pressure control function about which pressure levels would be best for gathering the additional data. Essentially, this is a check to make sure that analysis of the raw envelope data is likely to produce a reasonable curve fit. The raw envelope data would be considered to have a high quality if it has the normal physiological shape.

The quality algorithms of the invention may also be used to make a decision as to whether it is appropriate to publish the blood pressure values obtained. This would be a threshold test on the "overall" quality number. Control parameters (weights) may be set within the blood pressure algorithm to help with other aspects of the NIBP algorithm and improve the quality of the final published numbers. The quality algorithms may also help the system to decide whether to publish any warnings. When significant artifact is present, a warning should be given. This additional information would improve the quality of patient care because it could mean that another reading should be taken if high accuracy is needed. This could include many levels of warnings as appropriate to the quality level determined. This process would also be based on threshold tests using the "overall" quality number. At the end of the determination of blood pressure, the quality algorithm should provide an "overall" quality number which should be from 0 to 100, with 100 indicating excellent quality.

Figure 3A:
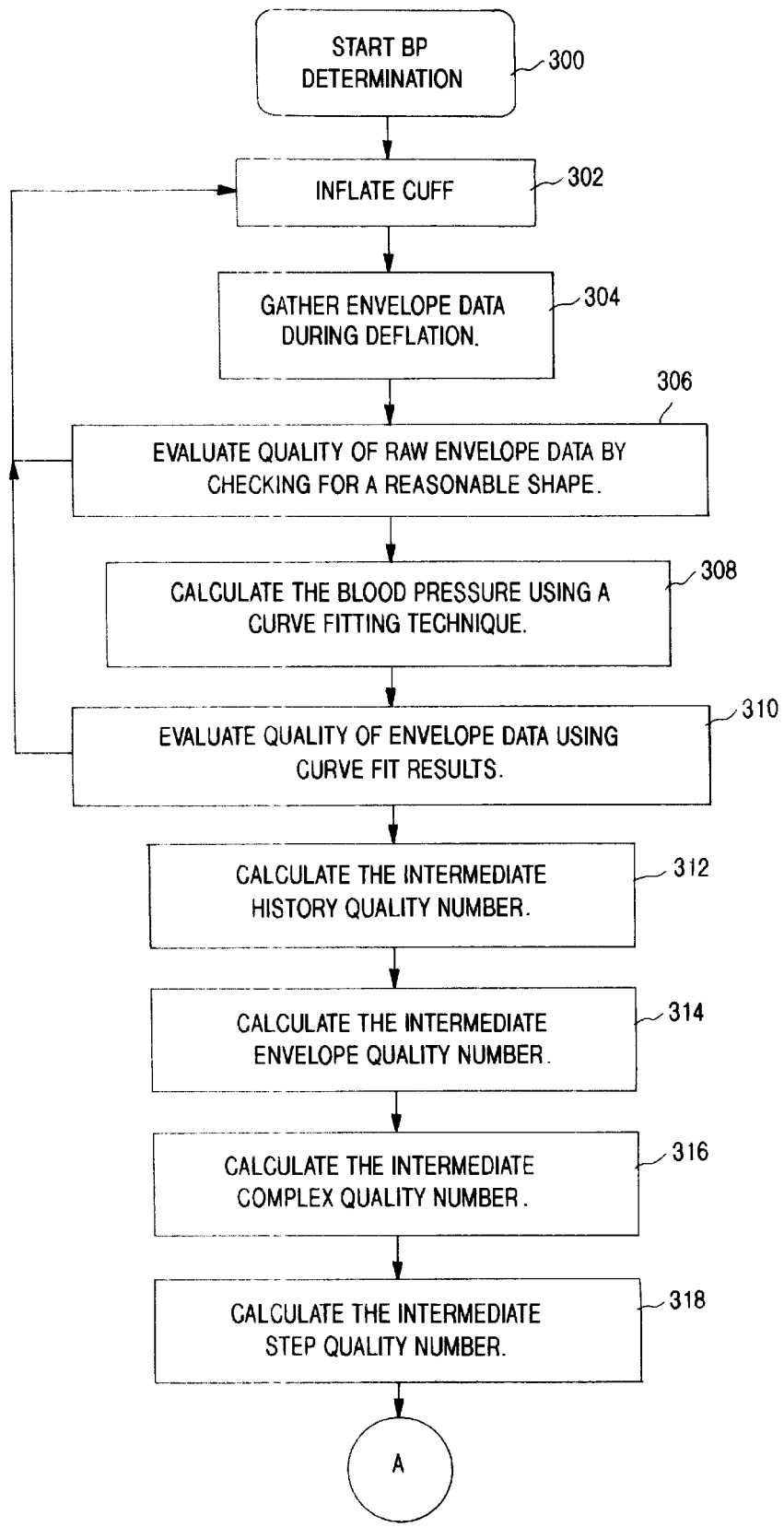
FIGS. 3A and 3B together constitute a flowchart which shows where quality calculations are performed during a conventional blood pressure determination in accordance with the techniques of the invention.
Figure 3B:
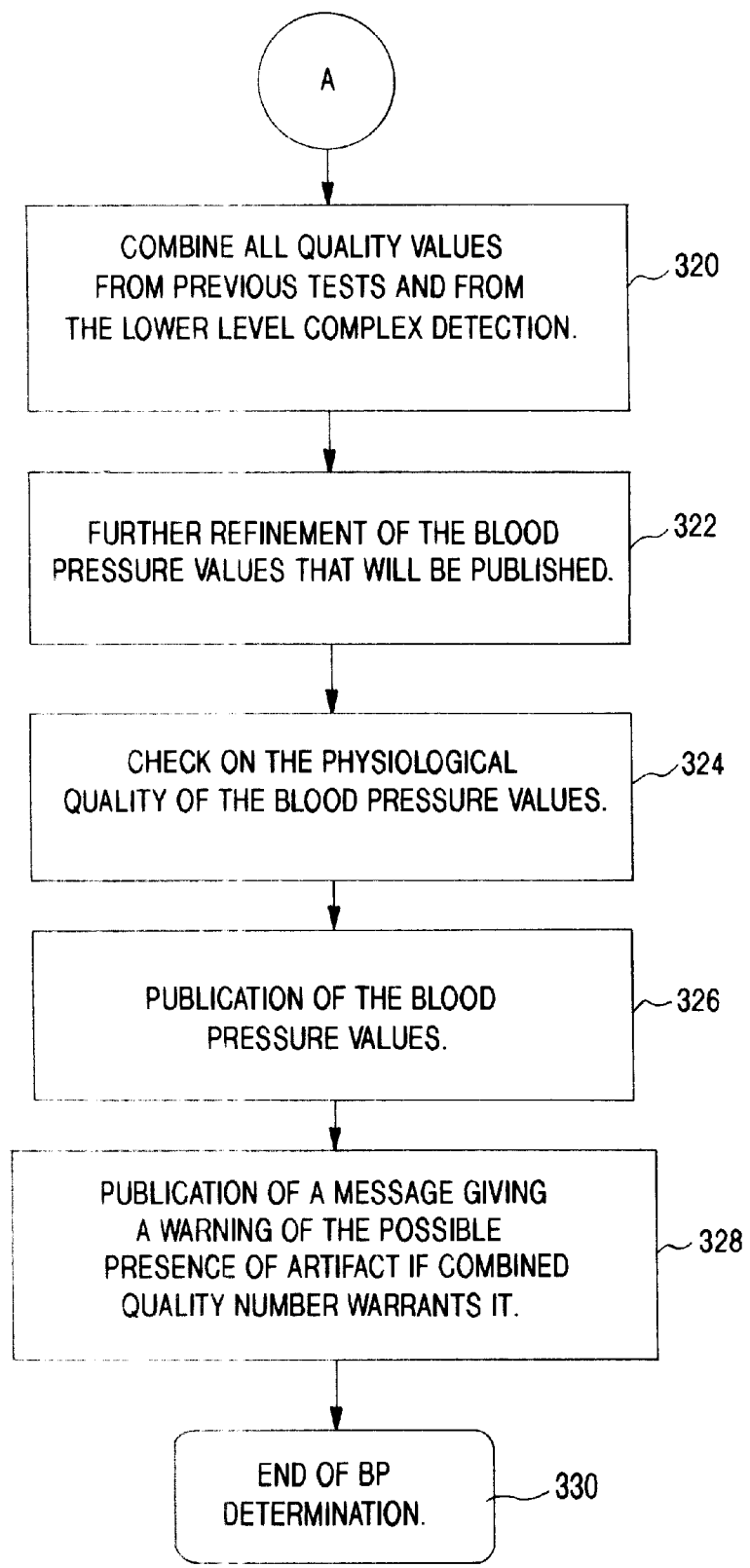

As shown in FIG. 3, the various algorithms which help improve NIBP quality are implemented at certain key times during a blood pressure determination. FIG. 3 illustrates an embodiment of a control algorithm(s) operating on microprocessor 107 in the apparatus of FIG. 1 in order to obtain a blood pressure measurement using the techniques of the invention. As shown, the blood pressure determination is started at step 300, and the blood pressure cuff 101 is inflated at step 302, typically to a point above systolic pressure for step deflation in a conventional manner. Envelope data is gathered during deflation of the cuff 101 in a conventional manner at step 304. Those skilled in the art will appreciate that the envelope has a complex size which is a function of the cuff pressure and that the complex size information is reduced to get the raw envelope data.

Figure 5:
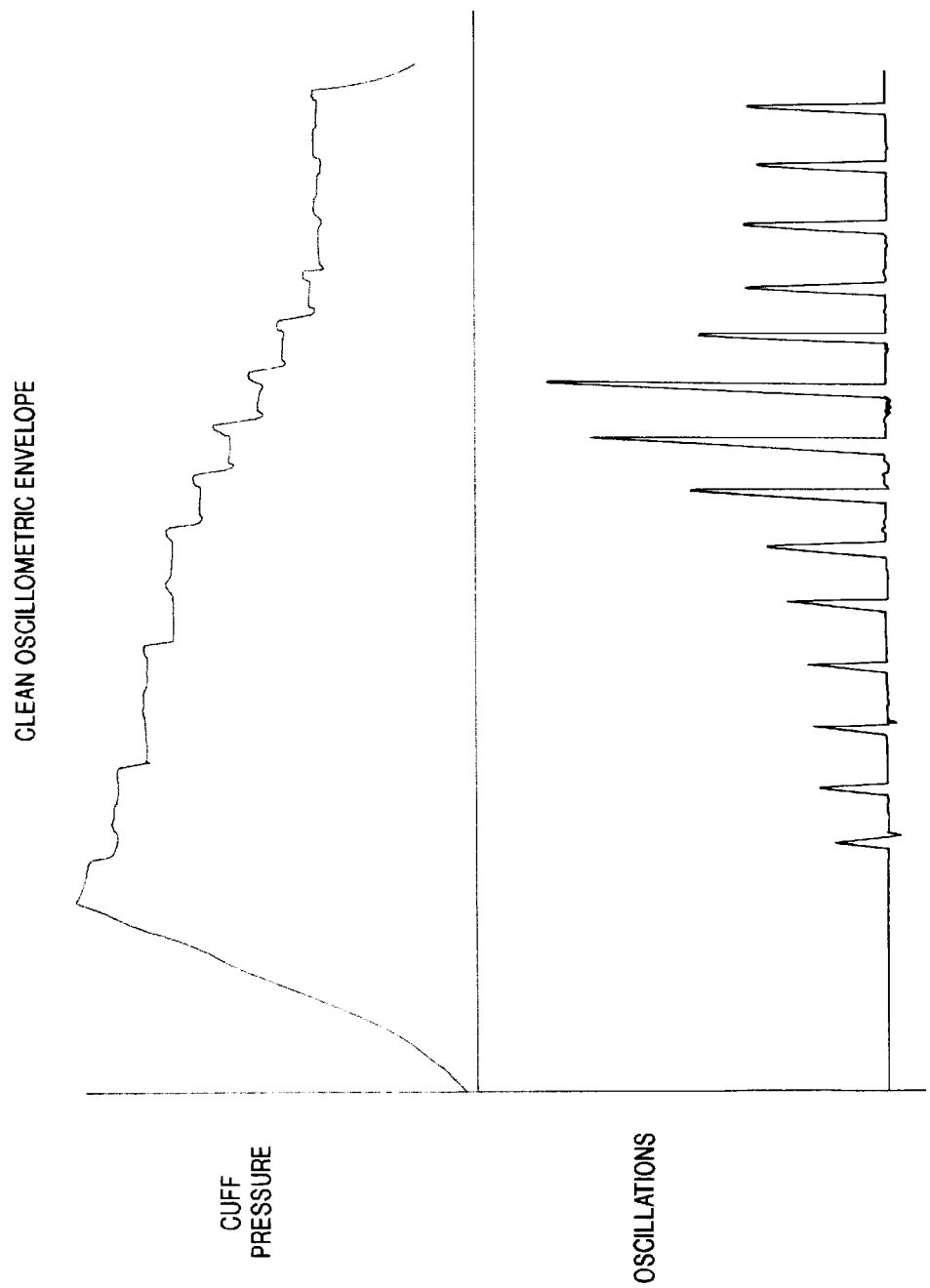
FIG. 5 is an example of an oscillometric blood pressure envelope with high quality, clean data.
Figure 6:
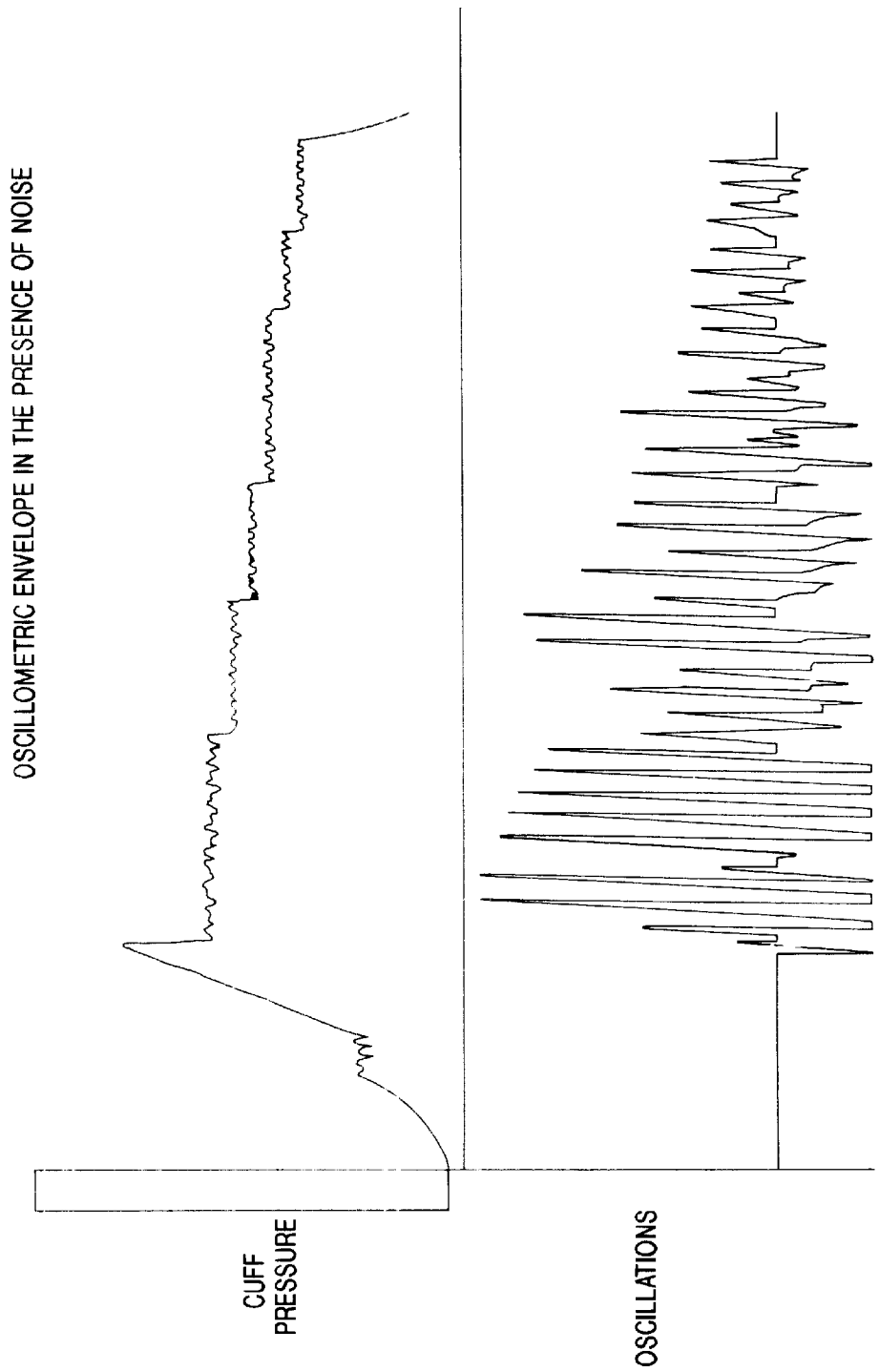
FIG. 6 is an example of an oscillometric blood pressure envelope including step deflate and complexes under artifact-ridden conditions.

In accordance with a preferred embodiment of the invention, once the raw envelope data is gathered at step 304, an evaluation of the quality of the raw envelope data is performed at step 306 before doing a curve fit analysis. FIG. 5 is an example of an oscillometric blood pressure envelope with high quality, clean data, while FIG. 6 is an example of an oscillometric blood pressure envelope including step deflate and complexes under artifact-ridden conditions.

At step 306, the algorithm determines the number of pressure levels on the high side and low side of the maximum oscillation amplitude in the raw envelope data. The algorithm should determine if there is balance in the envelope data before analysis should even be attempted. In other words, the algorithm determines whether the envelope data has the required general bell shape. This test would make sure there is a balance in the raw envelope data by simply sorting the data by pressure level, determining what pressure level has the maximum complex size, and then counting the number of points to either side of this maximum. A minimum number of points must be on either side of the maximum. If the raw envelope data has the usual physiological properties, and thus has a "reasonable shape" based on physiological expectations, the raw envelope data is allowed to undergo further analysis. This is the first "quality" check. The blood pressure is then calculated at step 308 using conventional techniques, such as the curve fitting technique described in U.S. Pat. No. 5,704,362 described above.

In the preferred embodiment of the invention, a second "quality" check is performed at step 310 to evaluate the quality of the raw envelope data after the curve fit or other blood pressure calculation using what was learned by doing the curve fit or blood pressure calculation. This test makes sure the envelope data is spread over the range of cuff pressure levels in a balanced manner. If the raw envelope data is close to the curve fit and the raw data has little noise, the quality indicator would go up. A set of intermediate quality values would be found and combined to get an "overall" quality. Other important information learned by doing the curve fit is where to best pick the blood pressure values and what complex size corresponds to each possible cuff pressure. An evaluation of the blood pressure numbers is performed to see if they make physiological sense (e.g., diastolic pressure<mean arterial pressure (MAP)<systolic pressure) and if the blood pressures are in a reasonable range. As the blood pressure numbers become less likely physiologically, the quality would go down.

Figure 7:
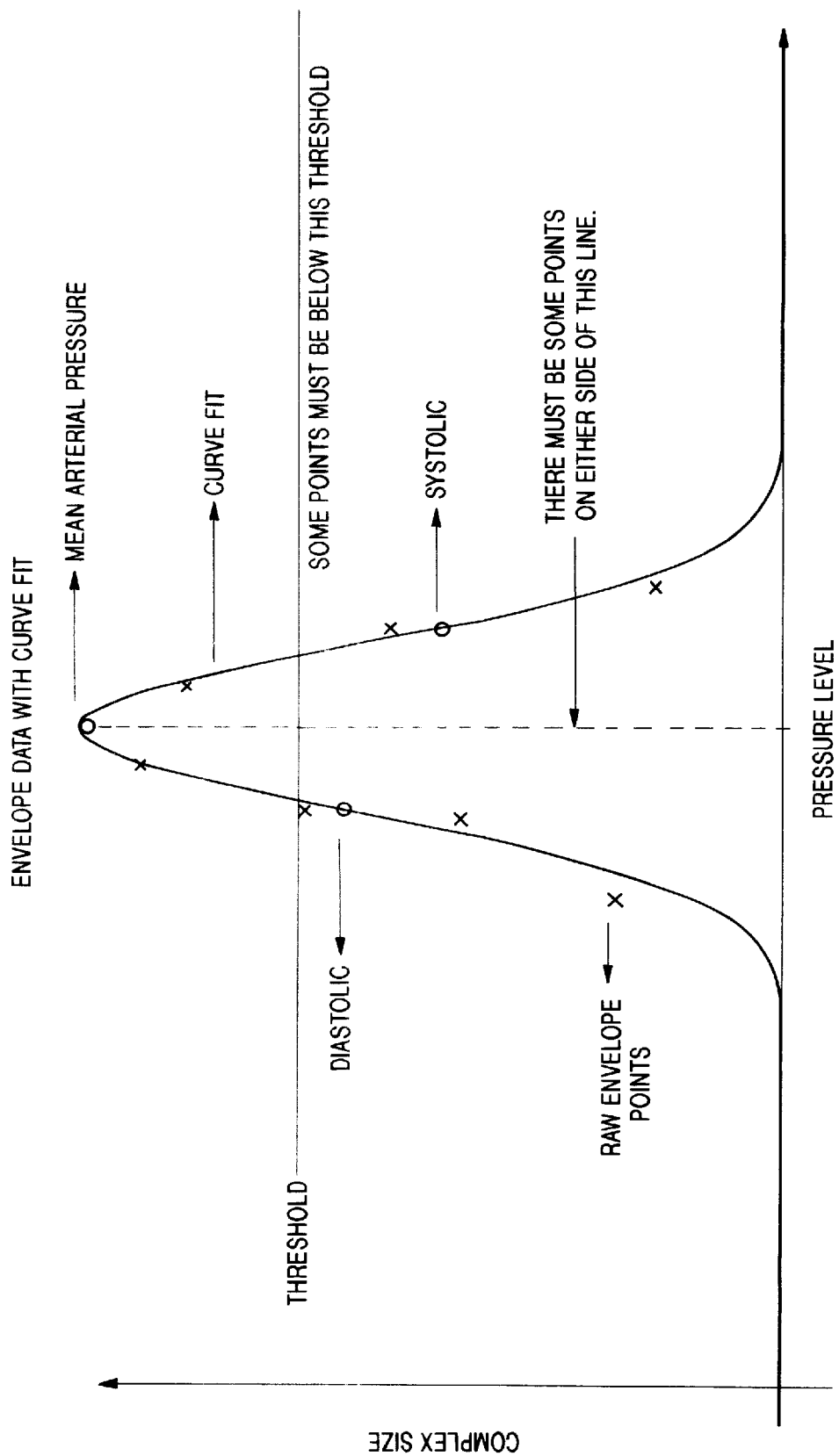
FIG. 7 illustrates an oscillometric blood pressure envelope with clean data including raw data points to either side of a maximum and data points below a designated threshold.
Figure 8:
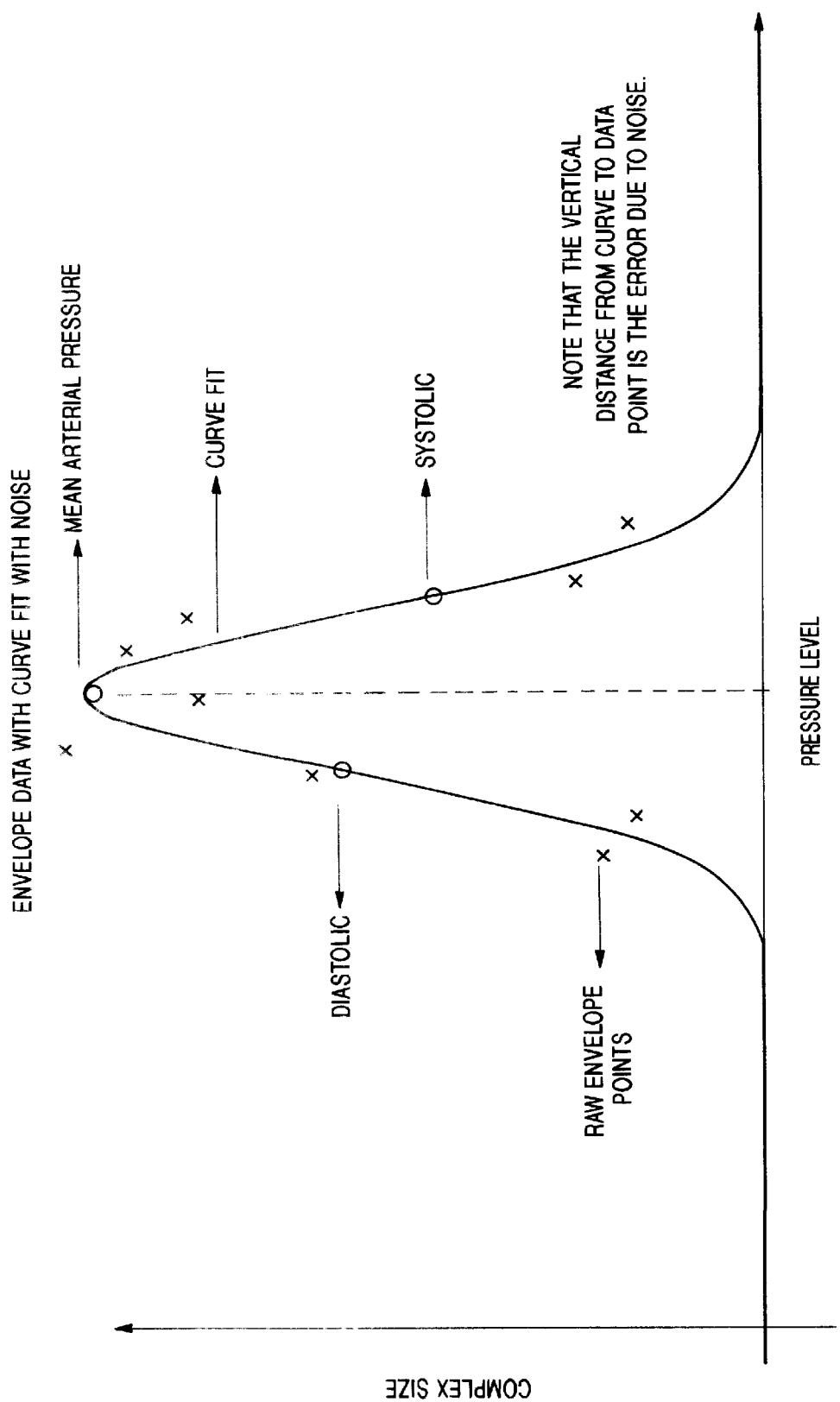
FIG. 8 illustrates the envelope of FIG. 7 after the data has been corrupted by noise.

By way of example, FIG. 7 illustrates an oscillometric blood pressure envelope derived from the clean data of FIG. 5 including raw data points to either side of a maximum and data points below a designated threshold. On the other hand, FIG. 8 illustrates the envelope of FIG. 7 after the data has been corrupted by noise. Since the raw envelope data in FIG. 7 is close to the curve fit and the raw data has little noise, the quality indicator is high in FIG. 7 and low in FIG. 8.

In particular, at step 310, the algorithm determines the number of pressure levels on the high side and low side of the MAP as obtained from an initial estimate of the blood pressure after the curve fit at step 308. This test would again help guarantee that there is some balance in the envelope data and that there are enough points on the systolic and diastolic sides of the envelope. At step 310, the algorithm also determines the number of pressure levels which have complex sizes that are below some fraction of the envelope (oscillation) size at the mean arterial pressure (MAP). That is, it should be determined that the envelope is decreasing as one moves away from the MAP value and that the analysis done was mathematically stable and physiologically meaningful. In addition, at step 310, the algorithm determines the number of steps which are near the estimated systolic and diastolic values. If raw data is close to the systolic and diastolic blood pressure values, there is more certainty that they are correct and the quality should be higher.

Once the quality of the envelope data is evaluated at step 310, the intermediate history quality number is calculated at step 312. The history quality number is based on a comparison of the new NIBP values to recent NIBP determinations stored in a BP history archive (element 410 in FIG. 4) accessible by the microprocessor 107. In particular, the intermediate history quality number is found at step 312 by comparing the blood pressure numbers to the values in the history archive 410. If the values in the history archive 410 are within a 5% error of the new blood pressure numbers, they are counted as good. The percentage of good comparison to all of the comparisons made is the intermediate history quality number. Table 1 below illustrates the calculation of the intermediate history quality number, where a weighting adjustment is made for the age of the entry into the history archive 410. More recent data is weighed heavier than older data. In the example, it is assumed that the blood pressure values from the curve fit procedure are 120/80(93).

TABLE 1

| Sys | MAP | Dias | Age Weight | Sys Good | Map Good | Dias Good | Possible Score | Actual Score |
|---|---|---|---|---|---|---|---|---|
| 130 | 96 | 81 | 7 | 0 | 7 | 7 | 21 | 14 |
| 127 | 98 | 85 | 5 | 0 | 0 | 0 | 15 | 0 |
| 131 | 96 | 80 | 5 | 0 | 5 | 5 | 15 | 10 |
| 124 | 98 | 70 | 3 | 3 | 0 | 0 | 9 | 3 |

TABLE 1-continued

| Sys | MAP | Dias | Age Weight | Sys Good | Map Good | Dias Good | Possible Score | Actual Score |
|-----|-----|------|------------|----------|----------|-----------|----------------|--------------|
| 117 | 94  | 79   | 1          | 1        | 1        | 1         | 3              | 3            |
| 135 | 103 | 81   | 1          | 0        | 0        | 1         | 3              | 1            |

The total possible score is 66, and the total actual score is 31. Therefore, the intermediate history number is 31/66, or 47 percent.

The BP history archive 410 is updated periodically to keep only the most recent information. If there are good comparisons to add to the history archive 410, then the quality is high. Information is only placed in the history archive 410 when it is determined to have very high quality. The history archive 410 could include the curve fit parameters, but this is not shown here.

Next, the intermediate envelope quality number is calculated at step 314 as a measure of how well the curve fit at step 308 represents the raw data. In calculating this number, an envelope sum squared error (s.s.e.) is preferably found using the following formula:

$$\text{Envelope s.s.e.} = \Sigma(a_i - A \cdot e^{-(p_{i-B})2/C})^2$$

where:

"$a_i$" and "$p_i$" represent the envelope data and correspond to step oscillation amplitude and step pressure, respectively;

"$i$" is an index used for the envelope step data; and

A, B, and C are the parameters for amplitude, mean, and deviation that came out of the curve fit procedure. As noted above, A, B and C are parameters for a Gaussian function, where "A" represents the amplitude, "B" represents the center position or mean, and "C" represents the control of the width or deviation of the Gaussian curve used to describe the envelope. More detail regarding these parameters may be found in U.S. Pat. No. 5,704,362 to Hersh et al., incorporated above by reference.

Once the envelope sum squared error (s.s.e.) is found, it can be used to calculate the intermediate envelope quality using the formula:

Intermediate envelope quality=$A*100/(A+\text{sqrt}(\text{WEIGHT}*\text{Envelope s.s.e.}))$ The weight number depends upon the intermediate history quality. If the history value is high, the weight is a low number; if the history quality is low, the weight is a larger number. The envelope's sum-squared error can be compared to the envelope size to get an intermediate quality number. If the sum-squared error is low relative to the envelope size, the quality should be high, and if the error is high relative to the envelope size, the quality should be low. This value can then be used as an indication that the curve fit worked.

At step 316, the intermediate complex quality number is calculated, which is a measure of the percentage of steps whose best complexes are above an estimated noise level. The noise level is the root mean square (r.m.s.) error of all the complexes and is based on the complex sum-squared error (s.s.e.), which is an estimate of the noise. In general, if this complex sum squared error is low, the quality is high. This calculation is:

$$\text{complex s.s.e.} = \sum_{i,j} (c_{ij} - A \cdot e^{-(p_i - B)^2/C})^2$$

Where:

$c_{ij}$ is the raw complex information and stands for complex size;

i indexes the pressure level;

j is the index for the complexes at the pressure level;

$p_i$ represents the step pressure;

A, B, and C are the parameters that came out of the curve fit procedure.

A comparison of the noise level to the signal level can be used to determine which steps are to be counted as good. Table 2 below gives an example of this comparison calculation.

TABLE 2

| Cuff Pressure Step | Size of Best Complexes | Noise Level with Multiplier | Good |
|--------------------|------------------------|-----------------------------|------|
| 120                | 101                    | 51*4                        | no   |
| 112                | 152                    | 51*4                        | no   |
| 104                | 271                    | 51*4                        | yes  |
| 96                 | 548                    | 51*4                        | yes  |
| 88                 | 763                    | 51*4                        | yes  |
| 80                 | 514                    | 51*4                        | yes  |
| 72                 | 247                    | 51*4                        | yes  |
| 64                 | 121                    | 51*4                        | no   |

Therefore, in this example, the intermediate complex quality is 5 out of 8 or 63 percent.

As is apparent from Table 2, if the size of the best complexes at each step is much higher than a multiple of the noise, the intermediate complex quality number goes The intermediate step quality number is calculated at step 318 as a measure of the variability of the sizes of complexes at a step and is calculated by comparing the absolute difference between each complex and what is the best estimate of complex size for the cuff pressure at which the complex occurs. The best estimate of the complex size at a step comes from the two complexes that match the best for that step. The percentage of good complexes relative to the total number of complexes is used as the intermediate step quality number. To evaluate whether a complex is good or not the ratio of the absolute difference and the estimated complex size is calculated. The acceptance threshold for this ration depends upon the history quality number and varies from 0.125 to 0.25. If the history is good, the threshold ratio used is lower. For example, Table 3 below shows how the calculation is done.

In the following illustrative, but artificial, example only a small number of measured complexes is given. In a real determination, the number of measured complexes for each cuff pressure would typically be bigger and include the complexes which are used to get the best complex size. There are 6 good complexes out of a possibility of 9. Therefore, for this example data, the intermediate step quality is 6/9 which is 67 percent.

TABLE 3

| Cuff Pressure | Measured Complex Size | Best Complex Size for Step | Absolute difference | Threshold Ratio Used | Ratio Calculated | Good Complex |
|---|---|---|---|---|---|---|
| 125 | 85  | 91  | 6  | 0.125 | 0.066 | yes |
| 117 | 191 | 225 | 34 | 0.125 | 0.151 | no  |
| 109 | 334 | 310 | 24 | 0.125 | 0.077 | yes |
| 101 | 450 | 425 | 25 | 0.125 | 0.059 | yes |
| 93  | 546 | 535 | 10 | 0.125 | 0.019 | yes |
| 85  | 403 | 420 | 17 | 0.125 | 0.040 | yes |
| 77  | 311 | 295 | 16 | 0.125 | 0.054 | yes |
| 69  | 169 | 200 | 31 | 0.125 | 0.155 | no  |
| 61  | 76  | 120 | 44 | 0.125 | 0.367 | no  |

Thus, if there is small complex size deviation at a step, the quality is high.

At step 320 (FIG. 3B), the quality values calculated at steps 312–318 and from the lower level complex detection are combined. Preferably, the quality values that result from each test are calibrated between 0 and 100 so that the values from each test may be readily combined. The overall quality number is based on a combination of the intermediate qualities. For example, if the history quality is 90 or greater, then the history quality is used; otherwise, the average of the step and complex intermediate qualities are taken as the overall quality. Further detail regarding step 320 will be provided below with respect to FIG. 4.

Figure 9:
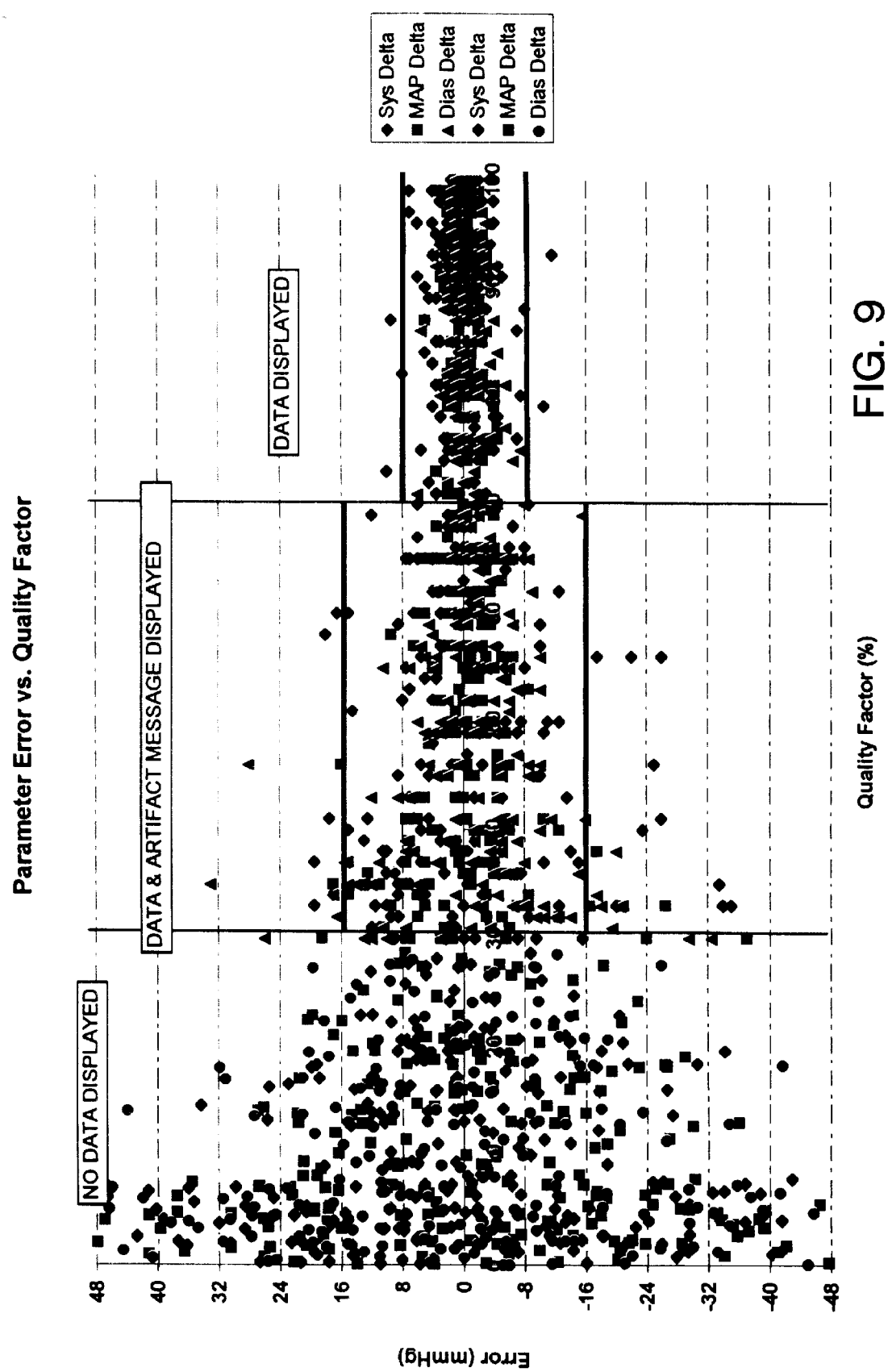
FIG. 9 illustrates how error in the determination of blood pressure numbers varies as a function of the quality factor.

Once the overall quality number is determined at step 320, further refinement of the blood pressure values that will be published to the viewer of the monitor display is performed at step 322. Conventional noise reduction algorithms may be used for this purpose, as necessary. The physiological quality of the blood pressure values is then checked at step 324 to determine if the final quality values actually make physiological sense and are in a reasonable physiological range. There is a further adjustment to the overall quality number at step 324 if the blood pressure numbers are very unusual physiologically. For example, as the blood pressure values get very high, a reduction of the overall quality is made. This helps to make sure that unusual values for blood pressure are only published when they are correct. The blood pressure values are then published at step 326 if the combined quality number is sufficiently high to establish that the data is reliable. In addition, a message may also be published at step 328 giving a warning of the possible presence of artifact if the combined quality number warrants such a message. For example, as shown in FIG. 9, different thresholds may be set for this purpose: no data is displayed for a low quality factor; the data may be displayed but with an artifact message for an intermediate quality factor; and the data may be displayed without a message for a high quality factor. The NIBP determination then concludes at step 330.

Those skilled in the art will appreciate that, in FIG. 3, steps 306, 310–320, 324, and 328 indicate the additions to the traditional NIBP algorithm in accordance with the techniques of the invention.

Figure 4:
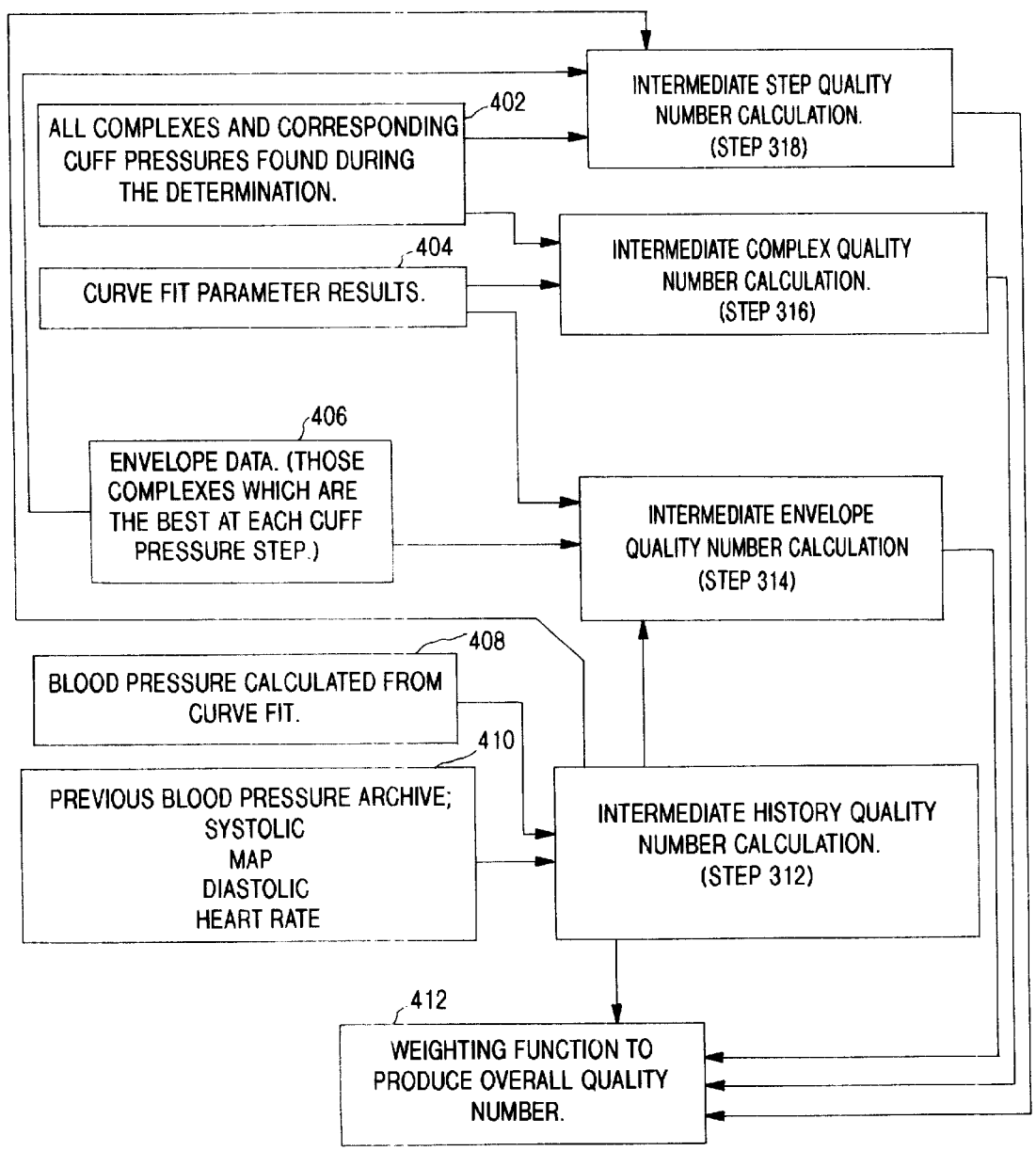
FIG. 4 is a flow chart showing how various calculated quality values are combined to get one overall quality value in accordance with the techniques of the invention.

FIG. 4 is a flow chart showing how various calculated quality values described above with respect to steps 312–318 in FIG. 3 are combined to get one overall quality value in accordance with the techniques of the invention. The data generated in steps 402–410 in FIG. 4 represent the types of data that are used in the quality calculations described above with respect to steps 312–318. In general, all derived data starts with complex and cuff pressure information. The purpose of FIG. 4 is to make clear how the intermediate quality numbers and the overall quality number are based on different data and concepts.

As illustrated in FIG. 4, five different types of data are generated:

1. The complex size and corresponding cuff pressure for all complexes that were found during the deflation part of the determination (step 402);
2. The curve fit result (i.e., the A, B, and C values) which can be used to calculate an expected complex size for a given cuff pressure level (step 404);
3. The envelope data, which is the set of complexes chosen for use as the best representation of a pressure step, where the envelope data is the complex size as a function of cuff pressure that will actually be used to calculate the blood pressure (step 406);
4. The blood pressure values calculated from the curve fit that will potentially be published (step 408); and
5. A history archive 410 of previous blood pressure values and curve fit parameters, e.g. systolic pressure, MAP, diastolic pressure, and heart rate.

These values are used in the quality calculations of steps 312–318 as indicated in FIG. 4. Then, at step 412, a weighting function is applied to the values calculated in at least steps 312–318 to produce an overall quality number. As noted above, this overall quality number is preferably between 0 and 100. The weighting function may be any predetermined weighting function set by a user or a weighting function set prior to device shipment.

As shown in FIG. 4, four intermediate quality values are calculated, including the step quality number, which is an indication of how much variability there is in complex size; the complex quality number, which is an indication of how the physiological signal and noise compare; the envelope quality number, which is an indication of how good the curve fit is; and history quality number, which is an indication of how consistent the blood pressure is with the recent past. Each of these numbers is preferably a value between 0 and 100. Once obtained, they are used in combination to get an overall quality number at step 412, and it is the overall quality number which is compared to thresholds to determine if the publication of the blood pressure values should take place and/or if a warning message should be additionally given (FIG. 9). Some of these intermediate quality numbers may be used in other ways. For example, as shown in FIG. 4, the intermediate history quality number is used in calculating the step and envelope quality numbers. Also, the intermediate quality numbers are used to determine if more data is needed before finishing a determination. The quality numbers can additionally be used to decide which numbers are put into the blood pressure determination archive.

It also will be appreciated by those skilled in the art that the foregoing has set forth an illustrative embodiment of the invention but that numerous alternative embodiments are possible without departing from the novel teachings of the invention.

For example, those skilled in the art will appreciate that the techniques of the invention may be used for blood pressure monitors in which the pressure is incremented from diastolic pressure as described, for example, in U.S. Pat. No. 4,461,266 to Hood et al. Also, those skilled in the art will appreciate that the techniques of the invention may be used for blood pressure monitors which do not use the amplitude matching techniques described by Ramsey et al. to determine whether oscillation complexes of sufficient quality have been received. The method of the invention can also be applied to blood pressure monitors using other techniques for measuring blood pressure besides the oscillometric method, such as the pulse wave velocity technique and the like. Accordingly, all such modifications are intended to be included within the scope of the appended claims.

We claim:

1. An automated sphygmomanometer apparatus, comprising:

an inflatable and deflatable pressure cuff;

an inflating apparatus coupled to said cuff so as to selectively apply a medium under pressure to said cuff for inflating and pressurizing said cuff;

a cuff pressure sensor coupled to said cuff so as to sense cuff pressure including any blood pressure oscillations therein;

a deflating apparatus coupled to said cuff so as to selectively relieve pressure from said cuff; and a programmed control device responsive to cuff pressure determination of said cuff pressure sensor, said control device programmed to control said inflating apparatus to inflate said cuff and said deflating apparatus to deflate said cuff during respective blood pressure determinations of a patient at predetermined intervals and to store oscillometric envelope data representing points of an oscillometric envelope defined by measured blood pressure oscillations, said control device further programmed to, to check the signal quality of said oscillometric envelope data, calculate the patient's blood pressure from said oscillometric envelope data if the quality of the oscillometric envelope data is good, and to selectively display the calculated blood pressure in accordance with the signal quality of said oscillometric envelope data.

2. An apparatus as in claim 1, wherein said programmed control device checks the signal quality of said oscillometric envelope data by determining if said oscillometric envelope has a predetermined general bell shape.

3. An apparatus as in claim 2, wherein said programmed control device calculates the patient's blood pressure using a curve fit procedure if said oscillometric envelope data has said predetermined general bell shape.

4. An apparatus as in claim 3, wherein said programmed control device checks the signal quality of said oscillometric envelope data by using blood pressure results determined during implementation of said curve fit procedure to said oscillometric envelope data to determine if the calculated blood pressures are in a reasonable physiological range and diastolic pressure<MAP<systolic pressure.

5. An apparatus as in claim 4, wherein said programmed control device checks the signal quality of said oscillometric envelope data by comparing newly acquired oscillometric envelope data with stored oscillometric envelope data and determining an intermediate history quality number as a percentage of values of said newly acquired oscillometric envelope data that are within a predetermined range from values of said stored oscillometric envelope data.

6. An apparatus as in claim 5, wherein said programmed control device weights more recent oscillometric envelope data more heavily than older oscillometric data during said determination of said intermediate history quality number.

7. An apparatus as in claim 5, wherein said programmed control device checks the signal quality of said oscillometric envelope data by determining an intermediate envelope quality number as a measure of how well curve fit data used by said curve fit procedure fits said newly acquired oscillometric envelope data.

8. An apparatus as in claim 7, wherein said programmed control device determines the intermediate envelope quality number using the equation:

Intermediate envelope quality=$A*100/(A+\text{sqrt}(\text{WEIGHT}*\text{Envelope s.s.e.}))$ where:

A is a Gaussian parameter for amplitude used by said curve fit procedure;

WEIGHT has a value based on said intermediate history quality number; and

Envelope sum-squared error (s.s.e.) is found using the following equation:

Envelope s.s.e.=$\Sigma(a_i-A\cdot e^{-(p_i-B)^2/C})^2$ where:

"$a_i$" and "$p_i$" represent the oscillometric envelope data and correspond to step oscillation amplitude and step pressure, respectively;

"i" is an index used for envelope step data; and

B and C are Gaussian parameters for mean, and deviation, respectively, used by said curve fit procedure.

9. An apparatus as in claim 7, wherein said programmed control device checks the signal quality of said oscillometric envelope data by determining an intermediate complex quality number as a measure of a percentage of pressure steps whose best complexes are above an estimated noise level that is a root mean square (r.m.s.) error of all complexes in said newly acquired oscillometric envelope data.

10. An apparatus as in claim 9, wherein said programmed control device bases said estimated noise level on a complex s.s.e. determined from the following equation:

$$\text{complex s.s.e.} = \sum_{i,j}\left(c_{ij} - A\cdot e^{-(p_i-B)^2/C}\right)^2$$

where:

$c_{ij}$ is complex data representing complex size from said newly acquired oscillometric envelope data;

"i" is an index used for envelope step data;

j is an index for the complexes at an envelope step pressure level;

$p_i$ represents step pressure; and

A, B, and C are Gaussian parameters for amplitude, mean, and deviation, respectively, used by said curve fit procedure.

11. An apparatus as in claim 9, wherein said programmed control device checks the signal quality of said oscillometric envelope data by determining an intermediate step quality number as a measure of the variability of sizes of complexes at an envelope step pressure level.

12. An apparatus as in claim 11, wherein said programmed control device determines said intermediate step quality number as a percentage of complexes out of all complexes received which has a ratio of an absolute difference between each complex to a best estimate of complex size for the cuff pressure at which the complex occurs which exceeds a threshold dependent upon said intermediate history quality number.

13. An apparatus as in claim 11, wherein said programmed control device combines said intermediate history quality number, said intermediate envelope quality number, said intermediate complex quality number, and said intermediate step quality number in accordance with a weighting function to create an overall quality number representative of the signal quality of said oscillometric envelope data.

14. An apparatus as in claim 13, wherein said programmed control device checks said calculated blood pressure and said overall quality number to determine if said calculated blood pressure and said overall quality number make physiological sense prior to displaying the calculated blood pressure.

15. An apparatus as in claim 14, wherein said programmed control device compares said overall quality number to a first threshold, whereby said calculated blood pressure is displayed only if said first threshold is exceeded.

16. An apparatus as in claim 15, wherein said programmed control device further compares said overall quality number to a second threshold, greater than said first threshold, whereby said calculated blood pressure is displayed with a message warning of artifact if said overall quality number exceeds said first threshold but not said second threshold and displays said calculated blood pressure without said warning message if said overall quality number exceeds both said first and second thresholds.

17. A method as in claim 13, wherein said signal quality checking step comprises the step of checking said calculated blood pressure and said overall quality number to determine if said calculated blood pressure and said overall quality number make physiological sense prior to displaying the calculated blood pressure.

18. A method as in claim 17, wherein said signal quality checking step comprises the step of comparing said overall quality number to a first threshold, whereby said calculated blood pressure is displayed in said displaying step only if said first threshold is exceeded.

19. A method as in claim 18, wherein said signal quality checking step further comprises the step of comparing said overall quality number to a second threshold, greater than said first threshold, and said displaying step comprises the steps of displaying said calculated blood pressure with a message warning of artifact if said overall quality number exceeds said first threshold but not said second threshold and displaying said calculated blood pressure without said warning message if said overall quality number exceeds both said first and second thresholds.

20. A method of measuring the blood pressure of a subject, comprising the steps of:
  obtaining from the subject a plurality of oscillometric data values including an amplitude from at least one complex taken at a plurality of pressure levels, said oscillometric data values representing points of an oscillometric envelope defined by measured blood pressure oscillations;
  checking the signal quality of said oscillometric data values by determining if said oscillometric envelope has a predetermined general bell shape;
  calculating the patient's blood pressure from said oscillometric data values when the signal quality is determined to be good;
  selectively displaying the calculated blood pressure in accordance with the signal quality of said oscillometric data values.

21. A method as in claim 17, wherein said step of determining if said oscillometric envelope has said predetermined general bell shape is conducted prior to said blood pressure calculating step, and said blood pressure calculating step comprises the step of calculating the patient's blood pressure using a curve fit procedure but only if said oscillometric envelope is determined to have said predetermined general bell shape.

22. A method as in claim 21, wherein said signal quality checking step comprises the step of using blood pressure results determined during implementation of said curve fit procedure to said oscillometric envelope data to determine if the calculated blood pressures are in a reasonable physiological range and diastolic pressure <MAP <systolic pressure.

23. A method as in claim 22, wherein said signal quality checking step comprises the steps of comparing newly acquired oscillometric envelope data with stored oscillometric envelope data and determining an intermediate history quality number as a percentage of values of said newly acquired oscillometric envelope data that are within a predetermined range from values of said stored oscillometric envelope data.

24. A method as in claim 23, wherein said signal quality checking step comprises the step of weighting more recent oscillometric envelope data more heavily than older oscillometric envelope data during said determination of said intermediate history quality number.

25. A method as in claim 23, wherein said signal quality checking step comprises the step of determining an intermediate envelope quality number as a measure of how well curve fit data used by said curve fit procedure fits said newly acquired oscillometric envelope data.

26. A method as in claim 25, wherein said step of determining said intermediate envelope quality number comprises the step of calculating the intermediate envelope quality number using the equation:

$$\text{Intermediate envelope quality} = A*100/(A+\text{sqrt}(\text{WEIGHT}*\text{Envelope s.s.e.}))$$

where:
  A is a Gaussian parameter for amplitude used by said curve fit procedure;
  WEIGHT has a value based on said intermediate history quality number; and
  Envelope sum-squared error (s.s.e.) is found using the following equation:

$$\text{Envelope s.s.e.} = \Sigma(a_i, 31\ A\cdot e^{-(pi-B)^{2/C}})^2$$

where:
  "$a_i$" and "$p_i$" represent the oscillometric envelope data and correspond to step oscillation amplitude and step pressure, respectively;
  "i" is an index used for envelope step data; and
  B and C are Gaussian parameters for mean, and deviation, respectively, used by said curve fit procedure.

27. A method as in claim 25, wherein said signal quality checking step comprises the step of determining an intermediate complex quality number as a measure of a percentage of pressure steps whose best complexes are above an estimated noise level that is a root mean square (r.m.s.) error of all complexes in said newly acquired oscillometric envelope data.

28. A method as in claim 27, wherein said step of determining said intermediate complex quality number comprises the step of calculating said estimated noise level based on a complex s.s.e. using the equation:

$$\text{complex s.s.e.} = \sum_{i,j} \left(c_{ij} - A \cdot e^{-(p_i - B)^2 / C}\right)^2$$

where:
- $c_{ij}$ is complex data representing complex size from said newly acquired oscillometric envelope data;
- "i" is an index used for envelope step data; and
- j is an index for the complexes at an envelope step pressure level;
- $p_i$ represents step pressure; and
- A, B, and C are Gaussian parameters for amplitude, mean, and deviation, respectively, used by said curve fit procedure.

29. A method as in claim 27, wherein said signal quality checking step comprises the step of determining an intermediate step quality number as a measure of the variability of sizes of complexes at an envelope step pressure level.

30. A method as in claim 29, wherein the step of determining said intermediate step quality number comprises the step of calculating a percentage of complexes out of all complexes received which has a ratio of an absolute difference between each complex to a best estimate of complex size for the cuff pressure at which the complex occurs which exceeds a threshold dependent upon said intermediate history quality number.

31. A method as in claim 29, wherein said signal quality checking step comprises the step of combining said intermediate history quality number, said intermediate envelope quality number, said intermediate complex quality number, and said intermediate step quality number in accordance with a weighting function to create an overall quality number representative of the signal quality of said oscillometric envelope data.

* * * * *

UNITED STATES PATENT AND TRADEMARK OFFICE
CERTIFICATE OF CORRECTION

PATENT NO. : 6,358,213 B1
DATED : March 19, 2002
INVENTOR(S) : Bruce Friedman, Lawrence T. Hersh and Richard Medero It is certified that error appears in the above-identified patent and that said Letters Patent is hereby corrected as shown below:

Column 9,
Line 26,
delete "Envelope s.s.e.=$\Sigma(a_i - A \cdot e^{(p_{i-B})2/C})^2$"
and insert -- Envelope s.s.e.= $\Sigma(a_i - A e^{-(p_i - B)^2 / C})^2$ --

Column 14,
Line 27,
delete "Envelope s.s.e.=$\Sigma(a_i - A \cdot e^{(p_{i\ B})2/C})^2$"
and insert -- Envelope s.s.e.= $\Sigma(a_i - A e^{-(p_i - B)^2 / C})^2$ --

Column 16,
Line 54,
delete "Envelope s.s.e.=$\Sigma(a_i - A \cdot e^{(p_{i-B})2/C})^2$"
and insert -- Envelope s.s.e.= $\Sigma(a_i - A e^{-(p_i - B)^2 / C})^2$ --

Signed and Sealed this

Twenty-first Day of January, 2003

JAMES E. ROGAN
*Director of the United States Patent and Trademark Office*